United States Patent
Hörmansdörfer

(10) Patent No.: US 8,206,454 B2
(45) Date of Patent: Jun. 26, 2012

(54) SELF-CUTTING SCREW-IN ELEMENT

(76) Inventor: Gerd Hörmansdörfer, Burgdorf-Beinhorn (DE)

( * ) Notice: Subject to any disclaimer, the term of this patent is extended or adjusted under 35 U.S.C. 154(b) by 1186 days.

(21) Appl. No.: 11/667,249

(22) PCT Filed: Nov. 9, 2005

(86) PCT No.: PCT/DE2005/002014
§ 371 (c)(1), (2), (4) Date: May 8, 2007

(87) PCT Pub. No.: WO2006/050708
PCT Pub. Date: May 18, 2006

(65) Prior Publication Data
US 2008/0025817 A1   Jan. 31, 2008

(30) Foreign Application Priority Data

Nov. 9, 2004 (DE) .......................... 10 2004 053 944
Nov. 30, 2004 (DE) .......................... 10 2004 057 709

(51) Int. Cl.
*A61F 2/32* (2006.01)
(52) U.S. Cl. ................. 623/22.31; 623/22.32; 623/22.21
(58) Field of Classification Search .... 623/22.21–22.39; A61F 2/32
See application file for complete search history.

(56) References Cited

U.S. PATENT DOCUMENTS

| | | | |
|---|---|---|---|
| 2,562,516 A | 7/1951 | Williams | |
| 4,653,486 A | 3/1987 | Coker | |
| 4,673,323 A | 6/1987 | Russo | |
| 4,715,859 A * | 12/1987 | Schelhas et al. | ........... 623/22.27 |
| 4,834,759 A | 5/1989 | Spotorno et al. | |
| 4,871,368 A | 10/1989 | Wagner | |
| 4,894,064 A | 1/1990 | Imhof | |
| 5,120,171 A | 6/1992 | Lasner | |
| 5,147,407 A * | 9/1992 | Tager | ......................... 623/22.27 |
| 5,458,649 A * | 10/1995 | Spotorno et al. | ........... 623/22.27 |

(Continued)

FOREIGN PATENT DOCUMENTS

CA    2 052 978    4/1992

(Continued)

OTHER PUBLICATIONS

German Search Report dated Apr. 11, 2007 in DE 10 2004 057 709.9 (with English translation of same).

(Continued)

*Primary Examiner* — Thomas J Sweet
*Assistant Examiner* — Jason-Dennis Stewart
(74) *Attorney, Agent, or Firm* — Collard & Roe, P.C.

(57) ABSTRACT

The present invention relates to a self-cutting screw-in element, e.g., an artificial hip joint socket, having a lateral surface which is at least partially curved or buckled in the threaded area, and a thread interrupted by at least one flute having a thread tooth profile tilted in the feed direction, in which the cutting edge formed between flute and thread tooth is displaced on the side of the thread tooth opposite to the feed direction, and/or in which the inclination or twist direction of the flute runs opposite to the twist direction of the thread and the inclination or twist angle of the flute is larger than the pitch angle of the thread. A design of this type is advantageous for specific applications because the forces necessary for screwing-in may thus be significantly reduced without disadvantageous effect on the other properties.

5 Claims, 2 Drawing Sheets

U.S. PATENT DOCUMENTS

| | | | |
|---|---|---|---|
| 5,628,630 | A | 5/1997 | Misch et al. |
| 5,997,578 | A | 12/1999 | Hoermansdoerfer |
| 6,146,425 | A | 11/2000 | Hörmansdörfer |
| 6,997,711 | B2 | 2/2006 | Miller |
| 7,513,913 | B2 | 4/2009 | Hoermansdoerfer |
| 2004/0121289 | A1 | 6/2004 | Miller |
| 2005/0038521 | A1 | 2/2005 | Hoermansdoerfer |
| 2009/0165611 | A1 | 7/2009 | Hoermansdoerfer |

FOREIGN PATENT DOCUMENTS

| | | |
|---|---|---|
| DE | 32 35 352 | 3/1984 |
| DE | 32 42 926 | 5/1984 |
| DE | 33 25 448 | 1/1985 |
| DE | 36 02 081 | 10/1986 |
| DE | 35 35 959 | 4/1987 |
| DE | 94 02 828 U | 6/1994 |
| DE | 298 14 010 | 11/1998 |
| DE | 197 57 799 | 7/1999 |
| EP | 0 358 345 | 3/1990 |
| EP | 0 480 551 | 4/1992 |
| EP | 0 622 058 | 11/1994 |
| EP | 0 898 470 | 3/1999 |
| FR | 1 118 057 | 5/1956 |
| FR | 2 548 012 | 1/1985 |
| FR | 2 622 432 | 5/1989 |
| JP | 61-217159 | 9/1986 |
| JP | 01-155845 | 6/1989 |
| JP | 07-217635 | 8/1995 |
| JP | 2001-502194 | 2/2001 |
| JP | 2004-011678 | 1/2004 |
| WO | 95/18586 | 7/1995 |
| WO | WO 97/39702 | 10/1997 |
| WO | 99/33416 | 7/1999 |
| WO | 00/75737 | 12/2000 |
| WO | 02/09688 | 2/2002 |

OTHER PUBLICATIONS

German Search Report dated Apr. 11, 2007 in DE 10 2004 053 944.8 (with English translation of same).

International Search Report, Nov. 4, 2007.

* cited by examiner

SELF-CUTTING SCREW-IN ELEMENT

CROSS REFERENCE TO RELATED APPLICATIONS

Applicant claims priority under 35 U.S.C. §119 of German Application No. 10 2004 053 944.8 filed Nov. 9, 2004, and German Application No. 10 2004 057 709.9 filed Nov. 30, 2004. Applicant also claims priority under 35 U.S.C. §365 of PCT/DE2005/002014 filed Nov. 9, 2005. The international application under PCT article 21(2) was not published in English.

The present invention relates to a screw-in element having a self-cutting thread, a peripheral thread rib being subdivided by at least one flute into thread teeth, and having at least one nonlinear lateral surface lying in a partial area of the thread extension, the thread tooth profile being tilted in the feed direction.

Threads are widely distributed as constructive elements of general mechanical engineering. Threads are typically shaped cylindrically. In addition, conical threads, e.g., for oil field pipes, are also in use. A large number of various thread profiles are known and defined in standards. The thread profile on a workpiece is typically unchanging, i.e., the thread profile at the thread beginning is identical to that at the thread end. However, exceptions are conceivable, in which a shape design of the thread profile formed by thread groove and thread tooth which changes flowingly may be advantageous in at least a partial area of the thread, e.g., to make the insertion of a screw thread into a nut thread easier.

Special geometric conditions in regard to the thread exist above all, however, in threads on curved surfaces, as occur in particular in artificial hip joint sockets which may be screwed in. For example, hypospherical, hemispherical, or hyperspherical, conical-spherical, parabolic toroidal, elliptical, and similar geometries are known in regard to the exterior shape of the shell body. In machining methods for producing threaded sockets of this type, flowingly changing distortions of the thread profile partially automatically result, which are neither intended nor desired in most cases. In particular if thread teeth having asymmetrical flanks (the particular lateral angles of the thread tooth profile) are used, the phenomenon results that depending on the tilt direction of the resulting thread tooth, the tooth height from the socket equator increases or decreases flowingly in the direction toward the socket pole, because of which thread teeth which are either much too large or nearly stunted result at the thread beginning near the pole. In the first case, the extremely large thread teeth result in very high forces being necessary for screwing in the socket, and/or the implant not being able to be screwed in up to complete bone contact. In the second case, only a very poor primary fixation will be achieved. In both cases, the danger of loosening of the implant exists, which would mean another operation on the patient as a consequence.

A further problem in screw-in elements having curved lateral surfaces is that the individual thread teeth do not dig into a correspondingly rasped out cavity—as frequently assumed—simultaneously or even with the thread beginning lying in front in the screwing direction first as they are screwed in. Rather, in spherical hip joint sockets having four thread rib revolutions, for example, the second revolution out, viewed from the equator digs in first, followed by the first and third revolution. Only when the cited three revolutions have already largely dug in does the fourth revolution come into contact with the cavity. Because the teeth of the first through third revolutions are automatically guided in the cut groove, the fourth thread revolution is subject to this compulsion in regard to its penetration direction. In a tilted thread tooth profile, a shift which is displaced onto one side of the thread tooth profile then arises.

It is known from computational models using finite elements that a more favorable load transfer between implant and bony bearing may be achieved by tilting the thread tooth over toward the socket pole. This results from the spatial position of the main load factor in the movement cycle while walking during the placement of the heel and the relative position of the implanted hip joint socket. If the thread tooth profile is tilted correspondingly in the direction toward the socket pole and the twist direction of the flute corresponds to the twist direction of the thread, as usual, the cutting edge formed on one side between thread tooth and flute in the direction toward the socket pole may not unfold its effect. An undesirably high value of the screw-in torque is the result of this problem.

The state of affairs described above is at least partially the subject matter of European Patent Specification EP 0 898 470 and is therefore generally known in the published framework. It is suggested in this publication that, to achieve a specific thread profile curve, the thread be implemented having a correspondingly tailored variation of the pitch in such a way that an identical thrust direction results during the screwing-in procedure for all teeth of the thread rib course. This design has already been used successfully in the field of medical technology in artificial hip joint sockets. The protective rights of the associated patent family are used exclusively by one producer. However, a lathe, whose CNC controller permits the programming of a variable thread pitch, is necessary for turning a screw-in element of this type.

Therefore, the object exists of providing alternative screw-in elements and/or screw-in elements (e.g., in the form of hip joint sockets) producible by machining even on older or not correspondingly equipped CNC machines, having a thread lying on a curved or angled lateral surface in at least a partial area having asymmetrical partial flank angles of the thread tooth and a reduced screw-in torque in relation to typical screw-in elements.

In a screw-in element having a self-cutting thread, the peripheral thread rib being divided by at least one flute into thread teeth, and having a nonlinear, in particular curved and/or buckled lateral surface lying in at least one partial area of the thread extension, the thread tooth profile being tilted in the feed direction, the object is achieved according to the present invention in that the flute intersects the thread teeth at an angle which runs opposite to the direction of the pitch angle of the thread.

In the screw-in element according to the present invention, the cutting edge formed between flute and thread tooth is displaced on the side of the thread tooth opposite to the feed direction, and/or the inclination or twist angle of the flute runs opposite to the twist direction of the thread and the twist angle of the flute is larger than the pitch angle of the thread. A design of this type is advantageous for specific applications because the forces necessary for screwing-in are thus significantly reduced without disadvantageous effects on the other properties.

The flute preferably runs diagonally in the screw-in element. In another preferred embodiment of the present invention, the flute has a twist. The cutting edge is more favorably situated on the rear flank of the screw-in element directed toward the equator. Furthermore, it is favorable for the twist angle and/or the inclination angle to be larger than the pitch angle of the thread. In another refinement of the present invention, the screw-in element is implemented as an implant and in a further preferred embodiment, it is implemented as in artificial hip joint socket.

Right-hand threads are standard in the field of technology. Left-hand threads are reserved for special applications, e.g., if loosening of the threaded connection is to be expected in the event of a correspondingly directed torsion stress, for example. Accordingly, the expectation of tightening a threaded connection to the right and loosening it to the left is generally deeply rooted. All screw lids and screw caps are designed accordingly, and also, for example, tapping screws. It is not different in screw-in elements (e.g., artificial hip joint sockets). If screw-in elements are designed as self-cutting by flutes, these flutes frequently run neutrally, i.e., having a twist angle of zero degrees. The cross-section of the particular thread tooth forms a cutting surface which stands very slightly positively because of the pitch angle of the thread. Many tapping sheet-metal screws have flutes which twist slightly to the left or run inclined slightly to the left, but which solely compensate for the pitch angle of the thread and have their cutting surface positioned neutrally. Left-hand flutes are known, for example, in taps which are to transport the chips arising during cutting in through threads away downward.

Right-hand threads are exclusively known in artificial hip joint sockets. The thread teeth are vertical to the socket axis in most products. If these hip joint sockets have a curved or buckled lateral contour, linearly running flutes, and a constant thread pitch, the forces during the screw-in procedure are at least theoretically uniformly distributed on the cutting surfaces formed by the flutes on the thread teeth and their more or less neutrally standing cutting edges. Because of the pressure (estimated: approximately 50 to 100 N) exerted by the operator in the axial direction during the screwing in, however, the cutting force is displaced more toward the cutting edge of the thread tooth lying toward the pole. It is then completely advisable to design this side as a cutting edge having a positive cutting angle, because the required force for screwing-in is thus significantly reducible. This may be implemented easily by a right-hand flute having a pronounced twist angle.

Up to this point, three artificial hip joint sockets having a left-directed flute with a curved lateral surface and neutral thread teeth have come onto the market. These are the model MC from Brehm, the model MT from Zimmer, and the model PAC from DePuy. In the first, the inclination angle is 15°, in the two others, 10°. The rake angle of the primarily acting cutting edge is then obtuse (referred to as "negative") and therefore results in unfavorably jamming, graining, and overall unacceptable cutting behavior.

The situation is very different if the thread tooth profile is inclined toward the pole with a curved lateral socket surface and constant thread pitch. The present applicant has recognized that the pole-side flank of the tooth slides along a cutting surface more or less without feed during the screwing in procedure, while the equator-side flank is fed radially away from the socket axis into the solid material. If the latter flank is equipped, using a left-directed twist or a left-directed inclination of the flute, and/or using a twist or inclination angle of the flute running opposite to the pitch angle of the thread, with cutting edges having a positive or strongly positive rake angle, the force needed for screwing in is very largely reduced. The cut is then smooth during screwing attempts into suitable hard foam, without edge breakouts and without the occurrence of graining. In addition, the tactiliance is now increased in such a way that the placement point of the implant may be felt without further measures.

For better understanding, the present invention is explained in greater detail in the following on the basis of three figures of the drawing. A hip joint socket shown in simplified form is used as a schematic example of a screw-in element having a curved lateral surface in FIGS. 1 and 2.

Figure 1:
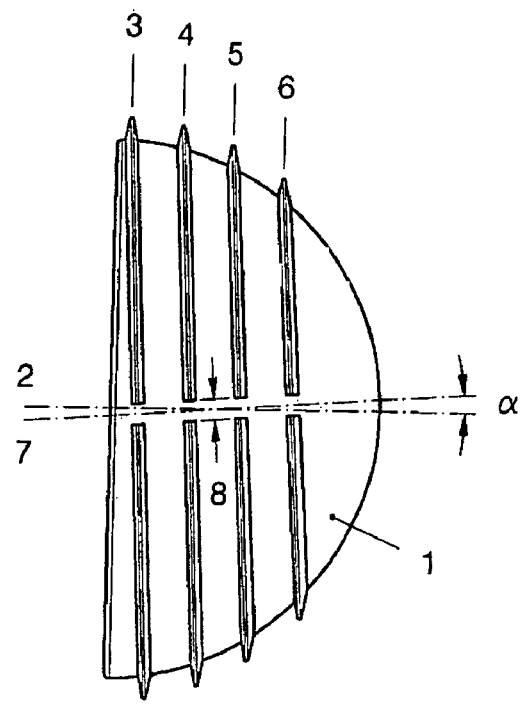
FIG. 1 shows an artificial hip joint socket having a thread according to the prior art.

FIG. 1 shows the schematic illustration of an artificial hip joint socket 1 according to the prior art in a slightly enlarged scale. The example shown has a spherical contour of the curved shell mantle. Four peripheral tooth ribs 3, 4, 5, and 6 are shown, which are interrupted by a single flute 8. The other flutes are left out for reasons of simplicity. The center axis of the hip joint socket is indicated by a dot-dash line 2 and the middle of the flute is indicated by a dot-dash line 7. The negative inclination angle α is formed between the two. The angular dimension of the inclination angle corresponds to the pitch angle of the thread, so that the cutting edges formed on the thread teeth by the flute stand transversely to the extension of the thread ribs in relation to the feed direction during screwing, and thus stand neutrally.

Figure 2:
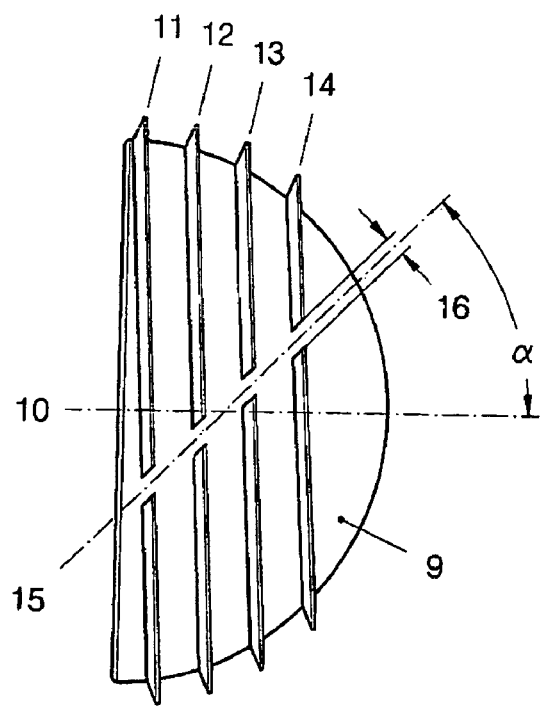
FIG. 2 shows a hip joint socket according to the present invention having a thread tooth profile tilted toward the socket pole and a negative inclination angle of the flute.

An artificial hip joint socket 9 according to the present invention of identical size and shape is illustrated in FIG. 2. As above, only a single flute 16 is shown for reasons of simplicity. The illustration of a twist has also been dispensed with because of the complexity of drawing it. The thread comprising four revolutions 11, 12, 13, and 14 has an asymmetrical tooth profile, which is inclined toward the socket pole. This tilt direction causes—as explained above—equalization of the forces to be transmitted between implant and bony bearing. The angle of the flute is opposite to that of the thread pitch. The flute encloses an angle α of 45° with its dot-dash center line 15 with the axis 10 of the hip joint socket. The cutting edges formed on the thread ribs are on the rear of the thread ribs on the thread tooth flanks directed toward the socket equator and each have a very positive rake angle because of the strongly diagonally running flutes. Due to the more favorable placement of the cutting edges than in the prior art, this is fully expressed in connection with the positive rake angle and thus causes a significant reduction of the screw-in torque and simultaneously an increase of the stripping reserve.

Figure 3:
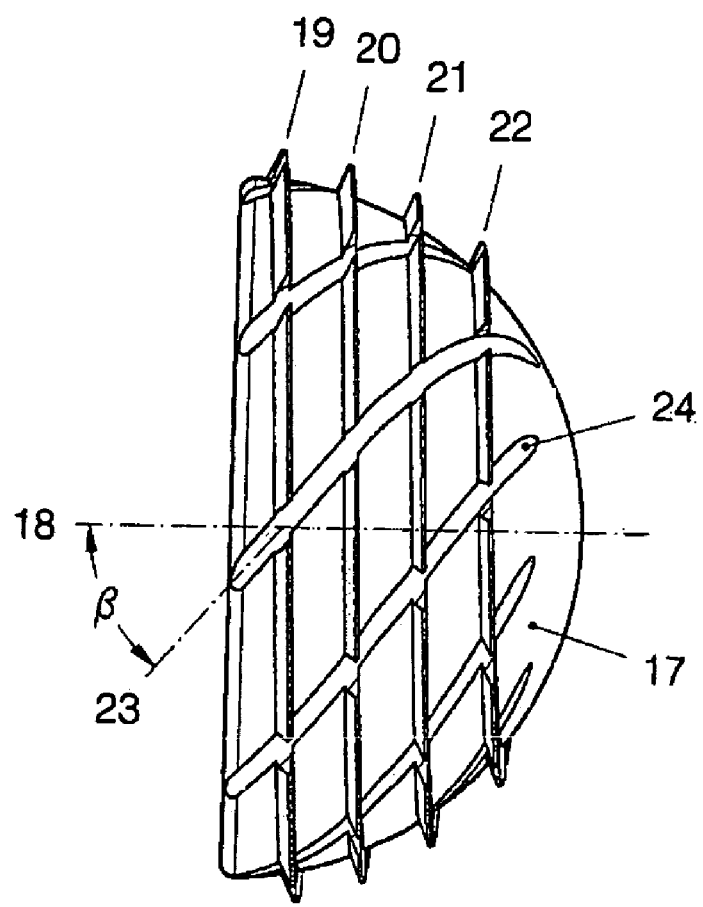
FIG. 3 shows a flute having a twist.

FIG. 3 also shows an artificial hip joint socket 17 according to the invention including a threading made up of four revolutions 19, 20, 21 and 22, and a twisted flute 24 enclosing a twist angle β with its dot-dash center line 23 with the socket axis 18.

Therefore, a screw-in element having a self-cutting thread having a curved and/or buckled lateral surface lying in the threaded area and a thread tooth profile tilted in the screwing direction is provided by the present invention, which, because of the inclination or twist direction of the flute opposing the twist direction of the thread, has significantly improved screw-in and stripping behavior and from which a reduction of the loosening rate may be expected. The screw-in element according to the present invention is producible without technical problems and without increased time consumption.

The invention claimed is:

1. A screw-in element having a self-cutting thread having a thread tooth profile, a peripheral thread rib being divided into thread teeth by at least one flute, and having a nonlinear lateral surface lying in at least one partial area of a thread extension, the thread tooth profile being tilted in a feed direction, wherein the at least one flute intersects the thread teeth at an angle which runs opposite to a direction of a pitch angle of the thread and of angular dimension larger than the pitch angle of the thread to form cutting first edges situated on respective rear flanks of the thread teeth and disposed at an acute angle relative to the rear flanks and second edges situated on respective front flanks of the thread teeth and disposed at an obtuse angle relative to the front flanks, the rear flanks being directed toward an equator of the screw-in element, the front flanks being directed toward the socket pole of the screw-in element, and wherein each cutting first edge of the cutting first edges is formed between the at least one flute and a respective thread tooth of the thread teeth and extends farther in the feed direction than the second edge extends in the feed direction so that each cutting first edge during a screwing-in procedure digs into bone before the second edge contacts the bone.

2. The screw-in element according to claim 1, wherein the at least one flute runs diagonally to a center axis of the screw-in element.

3. The screw-in element according to claim 1, wherein the at least one flute has a twist relative to a straight linear progression.

4. The screw-in element according to claim 1, wherein the screw-in element is implemented as an implant.

5. The screw-in element according to claim 4, wherein the screw-in element is implemented as an artificial hip joint socket.

* * * * *